United States Patent [19]
Davis et al.

[11] Patent Number: 5,207,665
[45] Date of Patent: * May 4, 1993

[54] ABSORBENT PRODUCT HAVING MECHANICAL ATTACHMENT MECHANISM

[75] Inventors: Martha Davis, New York, N.Y.; Daniel Formosa, Montvale, N.J.; Jeannie Gerth, Brooklyn, N.Y.; Patricia A. Moore, Montvale, N.J.; Stephen Russak, Hoboken, N.J.; Tamara Thomsen; Tucker Viemeister, both of New York, N.Y.

[73] Assignee: McNeil-PPC, Inc., Milltown, N.J.

[*] Notice: The portion of the term of this patent subsequent to Mar. 24, 2009 has been disclaimed.

[21] Appl. No.: 549,336

[22] Filed: Jul. 6, 1990

[51] Int. Cl.⁵ .............. A61F 13/15; A61F 13/20
[52] U.S. Cl. ................... 604/399; 604/402; 604/365; 604/385.1
[58] Field of Search ............ 604/385.1, 386, 387, 604/393, 395, 398, 399, 400, 401, 402, 365, 368, 367

[56] References Cited

U.S. PATENT DOCUMENTS

| | | | |
|---|---|---|---|
| 2,606,558 | 8/1952 | Kennette | 604/399 |
| 3,555,624 | 1/1971 | Koehn | 604/402 X |
| 3,566,870 | 3/1971 | Benjamin | 604/399 |
| 3,768,480 | 10/1973 | Mesek et al. | 604/365 |
| 3,788,323 | 1/1974 | Robinson | 604/402 X |
| 4,338,939 | 7/1982 | Daville | 604/399 |
| 4,880,419 | 11/1989 | Ness | 604/368 |

Primary Examiner—David Isabella
Assistant Examiner—Elizabeth M. Burke

[57] ABSTRACT

Absorbent products, such as sanitary napkins, are Provided which include mechanical attachment means for securing the undergarment-facing side of these products to an undergarment for minimizing shifting during movements by a wearer. The mechanical attachment means includes male and female fastening elements which engage to capture a portion of the thickness of the undergarment and may include slide fasteners, snap fasteners and fasteners including apertured rings with protruding button male portions.

25 Claims, 6 Drawing Sheets

ABSORBENT PRODUCT HAVING MECHANICAL ATTACHMENT MECHANISM

FIELD OF THE INVENTION

This invention relates to absorbent products for absorbing body fluids, and in particular, to means for applying such products against the perineal portion of the body and for holding them in place by securing them to the crotch portion of an undergarment. Such products find wide application as sanitary napkins, panty shields, panty liners and adult incontinence pads.

Background of the Invention

In order to insure that a sanitary napkin performs its function effectively, it is important for the absorbent surface of the product to be properly exposed to the fluid being absorbed. Maximum absorptive efficiency is achieved when the napkin conforms to the perineal area of the user's body and is urged against the user's body by the undergarment. In conventional sanitary napkins having wood pulp absorbent elements, the sizable bulk of the product aids in conforming the absorbing surface to the perineal area. With such products, longitudinally disposed, pressure-sensitive adhesive strips have generally provided adequate adherence to the undergarment.

However, recent advances in absorbent technology, such as thin absorbent layers containing superabsorbents or peat moss boards, have reduced the thickness of sanitary napkins and other absorbent products. The reduced cross-sectional area and bulk of these improved products results in less resistance to twisting, folding and bunching, thereby resulting in a loss of product effectiveness. As the user goes about ordinary movements, the napkin may become twisted or otherwise oriented in less than an optimal position. This condition causes both user discomfort and loss of absorptive efficiency.

Accordingly, there is a need for a retaining means for absorbent products, such as ultra-thin sanitary napkins, for keeping them in substantial conformance with both the perineal region of the body and the user's undergarment. Such a retaining means would thus reduce the twisting and disorientation that absorbent products undergo if held to the undergarment merely by strips of adhesive.

SUMMARY OF THE INVENTION

Sanitary napkins are provided by this invention which include a central absorbent element having a body-facing side and an undergarment-facing side. The central absorbent element includes mechanical attachment means for securing the sanitary napkin to an undergarment for minimizing shifting of the napkin during movements by a wearer. The mechanical attachment means of this invention includes male and female fastening elements which engage to capture a portion of the thickness of the undergarment.

Accordingly, secure attachment to undergarments is provided even when the mechanical attachment means of this invention is used in association with ultra-thin sanitary napkins. Because the securement mechanisms described herein attach to capture a portion of the "thickness" of the undergarment, rather than merely adhesively attaching to the undergarment's fabric surface, a more reliable securement is afforded.

This invention provides a number of mechanical attachment mechanisms that are both easy to use and cost effective to the manufacturer. In the more preferred embodiments described herein, mechanical attachment means are provided in which at least one of the male and female fastening elements is affixed to the undergarment-facing side of the central absorbent element and the other fastening element is affixed to a flexible retainer strap which extends laterally from one of the sides of the napkin. The flexible retainer strap is of sufficient length to extend around the undergarment to provide for engagement of the fastening elements.

The mechanical attachment means may alternatively include a break-off tab which defines a portion of the male or female fastening elements. Other attachment means discussed in the following description include a slide fastener in which the male fastening element comprises a circular protruding button and the female fastening element comprises an aperture means for receiving and slidably engaging the circular protruding button.

BRIEF DESCRIPTION OF THE DRAWINGS

The accompanying drawings illustrate preferred embodiments of the invention for the practical application of the principles thereof, and in which.

DETAILED DESCRIPTION OF THE INVENTION

This invention provides absorbent products, such as sanitary napkins, panty shields, panty liners and adult incontinence pads. The elements of the invention will be described, however, with respect to sanitary napkin embodiments in order to simplify the description. The term "sanitary napkin" is, therefore, used generically to include all absorbent products worn against the perineal area of the body.

The sanitary napkins of this invention include a central absorbent element having longitudinally extending sides, transverse ends, a body-facing side and an undergarment-facing side. The napkins further include a central absorbent element including mechanical attachment means for securing the napkin to an undergarment for minimizing shifting, bunching, and twisting during movements by a wearer. The mechanical attachment means of this invention includes one or more pairs of male and female fastening elements which engage to capture a portion of the thickness of the undergarment. As used herein, the term "thickness" refers to the cross-sectional thickness of the material of the undergarment.

In further detailed embodiments of this invention, sanitary napkins are provided in which at least one of the male and female fastening elements is affixed to the undergarment-facing side of the central absorbent and the other one of the male and female fastening elements is affixed to a flexible retainer means which extends laterally from one of the longitudinally extending sides or transverse ends of the sanitary napkin.

In further more detailed embodiments of this invention, an ultra-thin central absorbent element is provided having an absorbent layer therein having a thickness of less than about 5 mm and which comprises a plurality of longitudinally extending absorbent strips of a highly absorbent material, e.g., superabsorbent material or peat moss, disposed adjacent to one another. The absorbent layer also includes fibrous means for connecting the absorbent strips to one another for maintaining the integrity of the layer during handling. This embodiment also employs male and female fastening elements which can be engaged to capture a portion of the thickness of the undergarment.

This invention also provides a method of securing a sanitary napkin to an undergarment which includes providing a sanitary napkin having a central absorbent element including mechanical attachment means having male and female fastening elements. The method includes the steps of disposing the sanitary napkin onto an interior surface of an undergarment and engaging the male and female fastening element through a portion of the thickness of the undergarment so as to secure the sanitary napkin to the undergarment for minimizing shifting of the napkin during movements by a wearer.

With reference to the figures, and particularly FIGS. 1-4 thereof, there is shown a preferred sanitary napkin 16 being applied to an undergarment 14. This sanitary napkin 16 includes a body-facing side 24 and an undergarment-facing side 22, with absorbent material 34 disposed therebetween. The napkin 16 further includes mechanical attachment means comprising male and female fastening elements. In the preferred embodiment, the male fastening element comprises a circular protruding button 20. The female fastening element preferably comprises an apertured retainer ring 18, having radial slits 17 disposed about a circular aperture 19, which cooperate to snugly receive a thickness of the undergarment in conjunction with the circular protruding button 20. This invention is not, however, limited to male and female fastening elements having "circular" openings and cross-sections and can be practiced with elements having other geometric shapes, e.g. squares, ovals, rectangles, strips, or nongeometric shapes.

The preferred embodiment of FIGS. 1-4 further includes a flexible retainer means, preferably flexible strap 28 which extends laterally from one of the longitudinally extending sides or transverse ends of the napkin 16. As described in FIGS. 1-3, the flexible retainer is preferably a thermoplastic strap, for example, a strap including a woven or non-woven polyethylene web, which is affixed to the apertured retainer ring 18.

Figure 1:
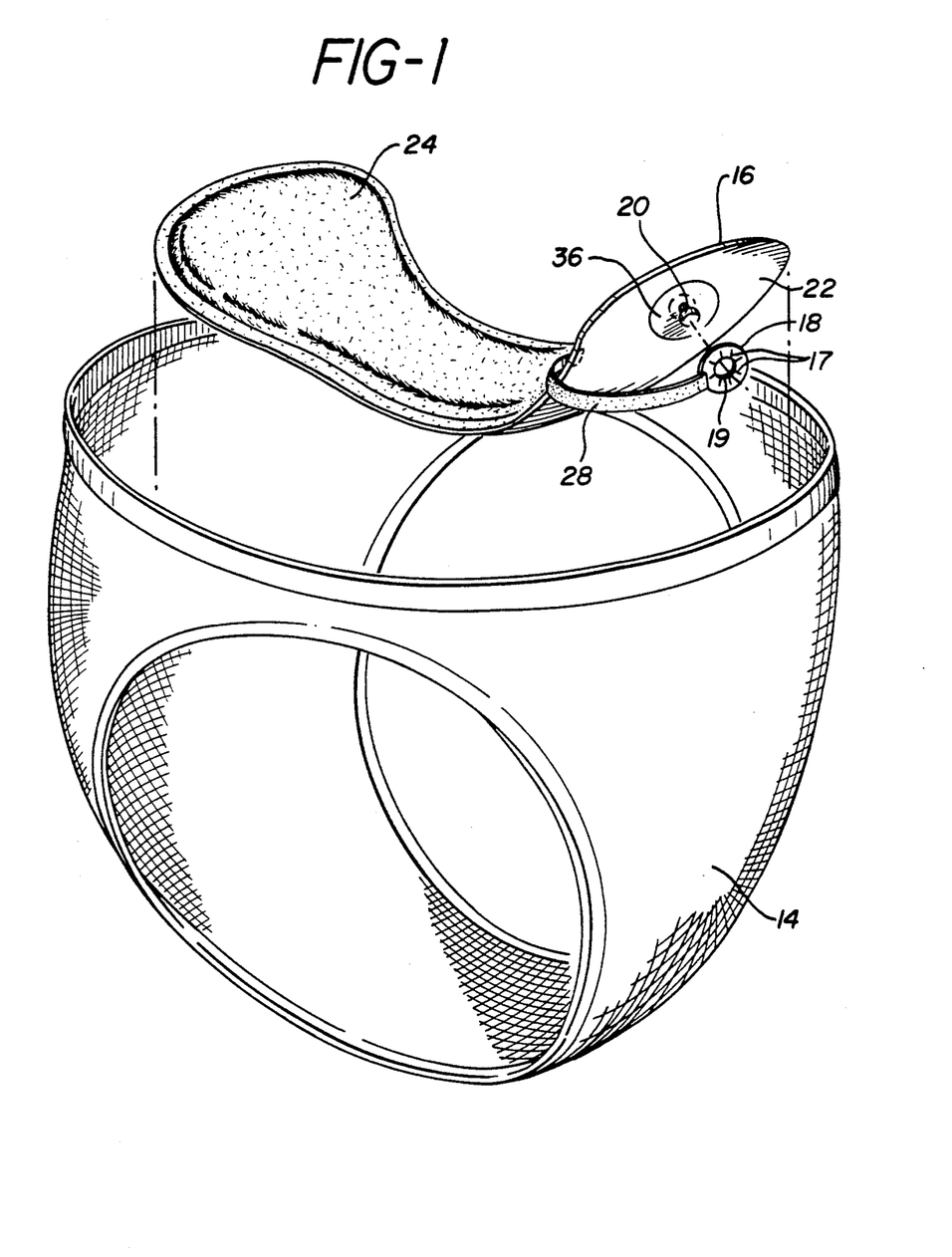
FIG. 1: is a perspective view of a preferred sanitary napkin having a mechanical attachment mechanism which includes a circular protruding button and apertured retainer ring.
Figure 2:
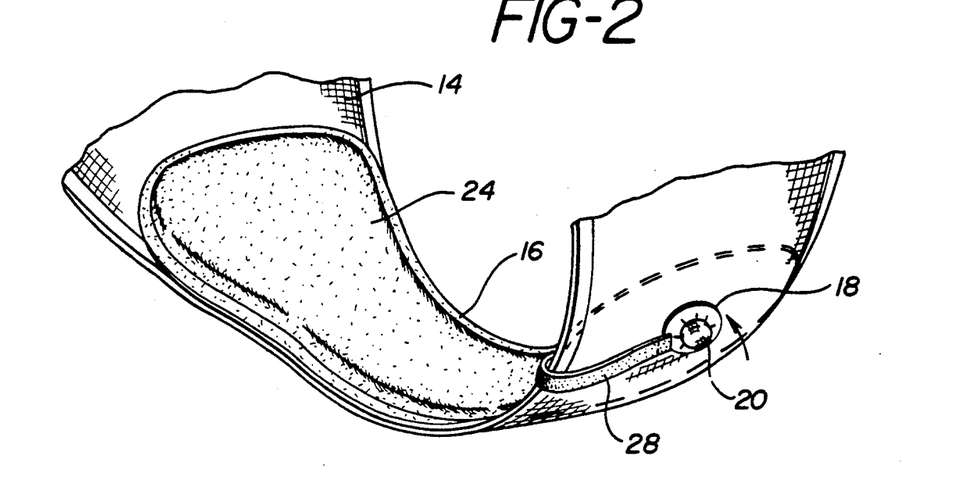
FIG. 2: is a partial perspective view of the undergarment and sanitary napkin of FIG. 1 illustrating how the sanitary napkin is mechanically attached to capture a portion of the thickness of the undergarment.
Figure 3:
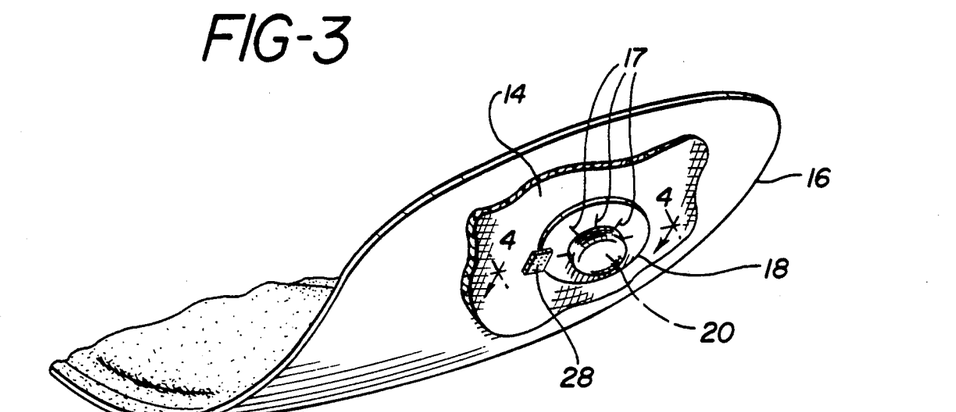
FIG. 3: is an enlarged partial perspective view of the sanitary napkin and undergarment of FIG. 2 more fully illustrating the attachment in detail.
Figure 4:
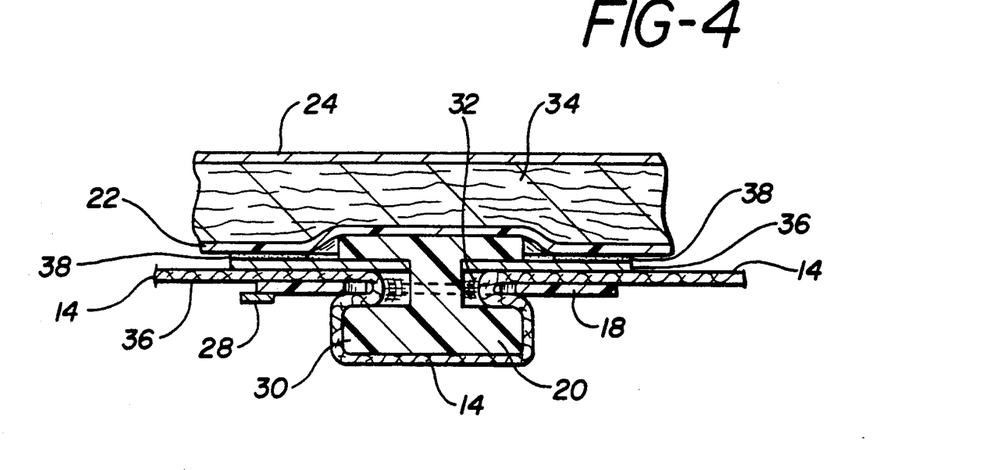
FIG. 4: is an enlarged cross-sectional view, taken through line 4—4 of FIG. 3, illustrating how the undergarment is secured to the circular protruding button with the apertured retainer ring.

As described in FIG. 4, the circular protruding button 20 includes a button portion 30 and a recess 32 for receiving the apertured retainer ring 18 and captured undergarment material. The circular protruding button 20 is preferably affixed to the undergarment-facing side 22 of the sanitary napkin 16 with circular tape 36 having adhesive element 38, although other types of attachment mechanisms will readily be apparent to those of ordinary skill. It is further noted that the undergarment 14 is not damaged in any way for the mechanical attachment means of this invention. The circular protruding button 20 and apertured retainer ring 18 provide sufficient clearance between them, such that upon engagement, the undergarment material 14 is snugly secured, but not severed or torn.

Figure 5:
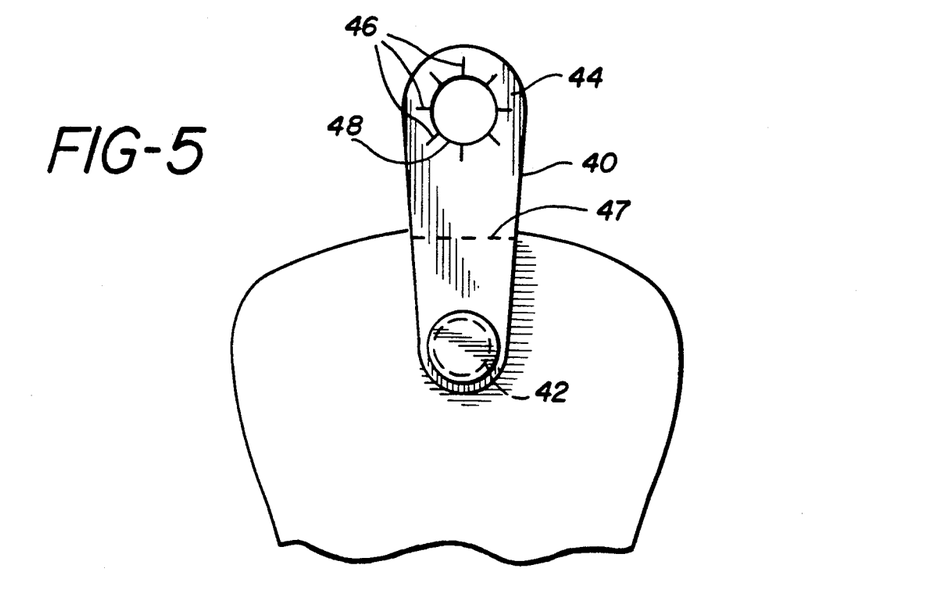
FIG. 5: is a partial plan view of an alternative sanitary napkin embodiment including a break-off tab which includes an apertured female portion.

With reference to FIG. 5, there is shown a partial view of another sanitary napkin embodiment in which a break-off tab 40 is provided, which preferably forms at least a portion of the male or female fastening elements. In this preferred embodiment, a circular protruding button 42 is provided on the lower portion of tab 40 and a female portion 44, which includes circular aperture 48 and radial slits 46, is disposed on the upper portion of the tab above the sever line 47.

Figure 6:
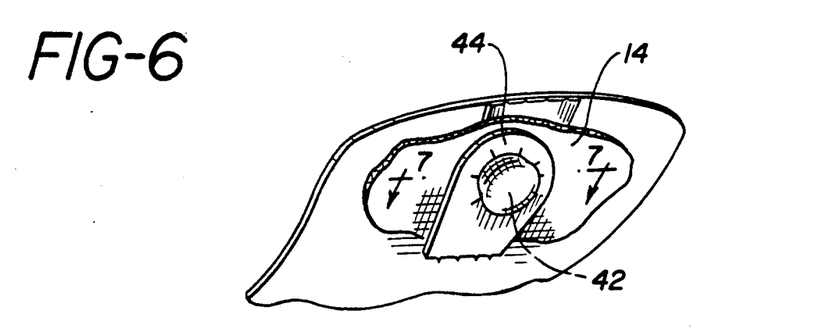
FIG. 6: is a partial perspective view of the sanitary napkin of FIG. 4, illustrating how the break-off tab has been severed and the female portion has been attached with the circular protruding button to capture a portion of the thickness of an undergarment.
Figure 7:
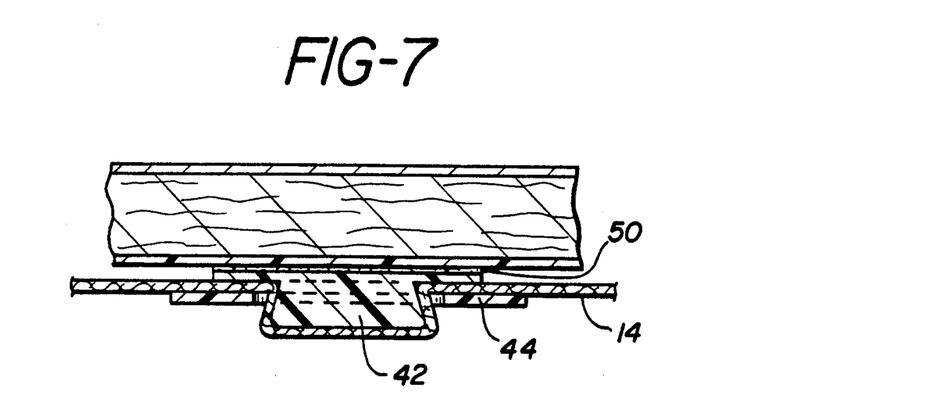
FIG. 7: is an enlarged cross-sectional view, taken through line 7—7 of FIG. 6, illustrating how the undergarment is captured between the apertured female portion and the circular protruding button of this embodiment.

According to FIG. 6, the female portion 44 is preferably broken along severe line 47 and joined with the circular protruding button 42 to capture a portion of the thickness of the undergarment 14. In the cross-sectional view of FIG. 7, the severed female portion is shown trapping the undergarment material for securing the sanitary napkin. In this view, the circular protruding button 42 is affixed to the undergarment-facing side of the napkin with adhesive 50. It is further understood that the lower portion of circular protruding button 42 can also be mounted beneath the undergarment-facing side of this and the other napkin embodiments of this invention.

Figure 8:
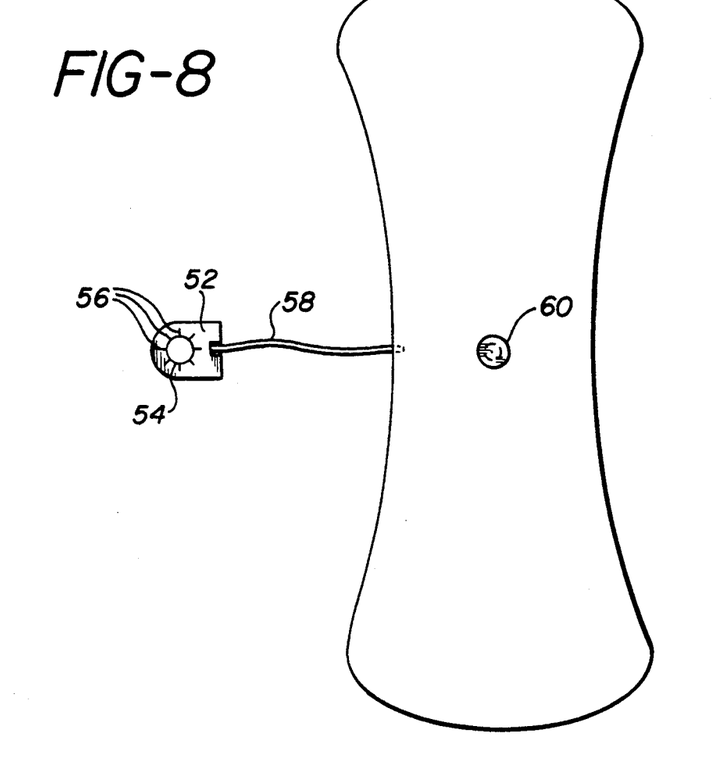
FIG. 8: is a plan view of a further sanitary napkin embodiment of this invention illustrating a circular protruding button affixed to an undergarment-facing side of the napkin and a female portion extending from a longitudinally extending side of the sanitary napkin by an elastic cord.
Figures 9, 10:
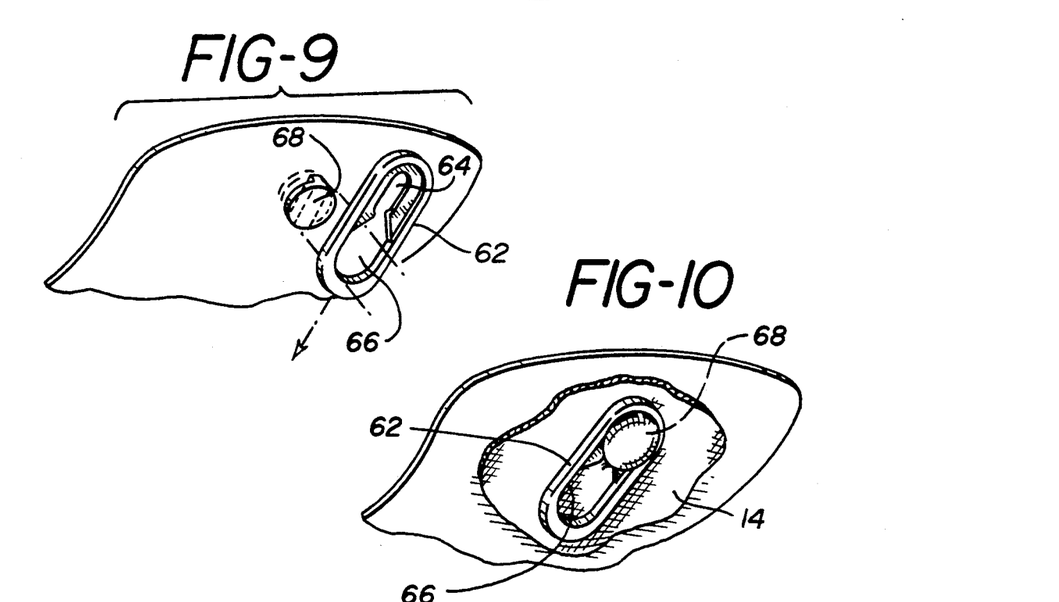
FIG. 9: is a partial perspective view of a further sanitary napkin embodiment including a slide fastener having a female fastening element and a male circular protruding button fastening element.
FIG. 10: is a further partial perspective view of the sanitary napkin embodiment of FIG. 9 illustrating how the female and male fastening elements are slidably engaged to capture a portion of the thickness of an undergarment.

In FIG. 8, there is shown another sanitary napkin embodiment having a circular protruding button 60 attached to an undergarment-facing side of a sanitary napkin. The mechanical attachment means of this embodiment further includes tab means, preferably a thermoplastic, female portion 52 having a circular aperture 54 and cooperating radial slits 56. The female portion 52 is preferably attached to a lateral side of this napkin with an elastic cord 58. By attaching the female fastening element with a flexible strap 28 or elastic cord 58, an advantage is obtained over the embodiments of FIGS. 5-7, 9 and 10, since the napkin can be discarded after use as a unitary structure without the inconvenience of accounting for a plurality of discrete elements. With reference to FIGS. 9 and 10, there is shown still another sanitary napkin embodiment including a circular protruding button 68 and a female fastening element 62 having aperture means for receiving and slidably engaging the circular protruding button 68. Preferably the aperture means includes a receiving portion 66 and restrictive portion 64. As illustrated in FIG. 10, the female fastening element 62 is disposed over the circular protruding button 60 through the receiving portion 66 of the aperture means to capture a portion of the thickness of the undergarment 14 in the restrictive portion 64.

Figure 11:
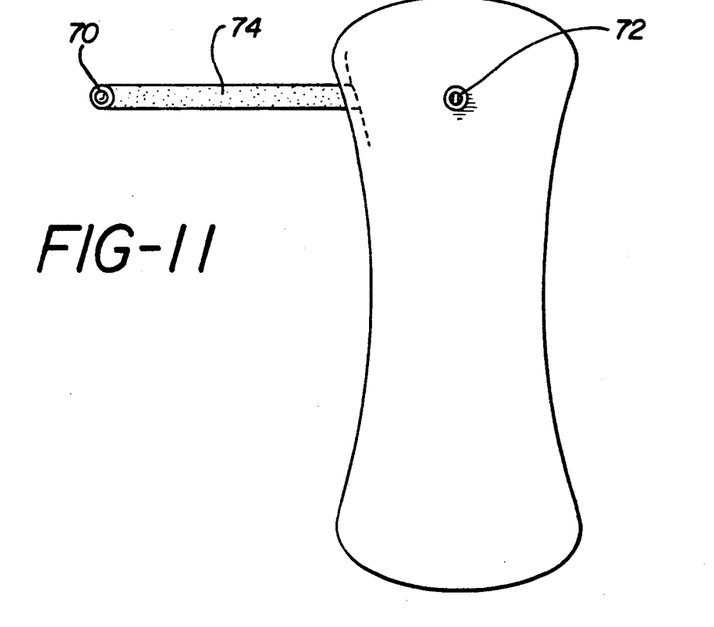
FIG. 11: is a further sanitary napkin embodiment of this invention having male and female fastening elements, whereby a female snap fastening element is affixed to the undergarment-facing side of the sanitary napkin and the male fastening element is affixed to a strap retainer extending laterally from a longitudinally extending side of the sanitary napkin.
Figure 12:
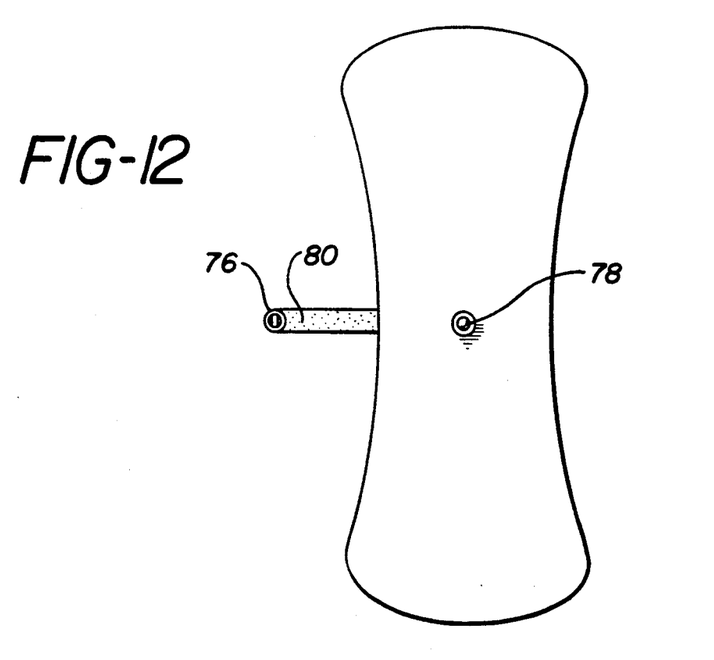
FIG. 12: is a plan view of a further sanitary napkin embodiment also including male and female snap fastening elements, whereby the male fastening element is affixed to the undergarment-facing side of the sanitary napkin and the female fastening element is affixed to a strap retainer extending laterally from a longitudinally extending side of the napkin.

Further embodiments of this invention are described in FIGS. 11 and 12, wherein conventional metal or plastic snap fasteners are employed to create mechanical attachment means. In FIG. 11, a female fastening element 72 of the snap fastener is affixed to an undergarment-facing side of the sanitary napkin, and a male fastening element 70 is affixed to the end portion of flexible strap 74, which preferably is a woven or non-woven web of polyethylene adhesively attached or heat sealed to a longitudinally extending side of the napkin. FIG. 12 illustrates a sanitary napkin embodiment also including commercial snap fasteners, in which a male fastening element 78 is affixed to the undergarment-facing side of the sanitary napkin and the female fastening element 76 is attached to a flexible strap 80, also preferably constructed of a polyethylene web. The construction and preferred materials for manufacturing the sanitary napkins of this invention will now be described.

The central absorbent elements of this invention may be constructed with any of the well known absorbent materials used in products for absorbing body fluids such as for example, loosely associated absorbent hydrophilic material such as cellulose fibers, e.g., wood pump, regenerated cellulose or cotton fibers. Such fibers may be chemically or physically modified and the absorbent element may include such fibers in combination with other materials, both natural, such as sphagnum moss, and synthetic, such as hydrophilic foams, hydrophilic polymers or the like.

The central absorbent element may also comprise layers of materials which in the aggregate are body fluid absorbent. For example, the outermost layer (closest to the body) may be a resilient, relatively non-absorbing, fluid previous material. Such a material is provided for comfort and conformability and directs fluid to an underlying layer, e.g. peat moss board or wood pulp, which retains such fluid. A useful material for this outer layer is hollow polyester fibers having a denier of about 8.5 and a length of about 1.5 inches.

Overlying the body-facing side of the central absorbent elements of this invention preferably is a fluid permeable cover material. This cover material may comprise any of the well known liquid pervious materials used in sanitary napkins including, for example, non-woven fabrics of cellulose, regenerated cellulose, polyester, polyethylene, or other synthetic polymers. Additionally, polymeric fibers or films having apertures therethrough to render the materials pervious to fluids may also by employed. A cover material of choice is a fabric comprising heat bondable polyester/-polyethylene conjugate fibers.

The central absorbent element, in accordance with a traditional design, can be wrapped in and adhered to an elongated C-shaped wrap or cover of fluid impervious material. See, U.S. Pat. No. 4,701,178 (FIG. 2) which patent is hereby incorporated by reference. The fluid impervious material preferably comprises a polyethylene "boat" which is adhered to the central absorbent element by an emulsion adhesive. The purpose of the polyethylene boat is fluid containment, whereby fluid will not be transferred from the undergarment-facing side and edges of the central absorbent element to an outer location where it could stain the undergarments of the user. The preferred polyethylene boat extends beyond the longitudinal ends of the central absorbent element. The boat is preferably heat or sonically sealed at the ends and adhered to a body fluid impervious barrier which constitutes the undergarment-facing side of the napkins. The barrier is provided to preclude body fluid from passing onto the undergarment of the wearer. The barrier, like the boat, may be any polymeric film such as a polyethylene, polypropylene, or cellophane or may be a normally fluid-pervious material that has been treated to be impervious such as a fluid repellent paper. When the boat and the barrier are made of heat bondable materials the boat may be advantageously thermally or ultrasonically sealed at its ends and to the barrier.

The preferred napkins of this invention can also include flaps, or side panels, which preferably extend out from the longitudinal edges of the barrier. The flaps can include absorbent and barrier layers and preferably extend a sufficient degree to enable them to overlie the outer crotch portion of the wearer's undergarment. They may also be constructed of a sufficient lateral length so that they overlap each other after they are wrapped around the crotch area of the undergarment. With flaps extended in this fashion, adhesive elements attached to the flap or flaps can be used to attach the flaps to one another. See U.S. Pat. No. 4,608,047, which is herein incorporated by reference. Flaps protect the user's undergarment from liquid escaping from the central absorbent element along its longitudinal edges and to act as an attachment system, in conjunction with the mechanical attachment means of this invention, to hold the central absorbent element firmly in place as it moves together with the crotch of the undergarment during the wearer's movements.

When the absorbent layer and the barrier material of the central absorbent element are both formed of thermoplastic material as described above, the napkin may be advantageously assembled by heat sealing or ultrasonic sealing. The absorbent layer of the flaps preferably is thermally sealed to the opposing longitudinal edges of the cover, and the barrier material of the flaps is thermally sealed to the opposing edges of the barrier of the central absorbent element. In a preferred embodiment, the barrier and the barrier material comprise sheets of 1.5 mil, embossed polyethylene.

The preferred adhesive elements of this invention preferably include pressure-sensitive adhesive. While such adhesive means are illustrated in the form of longitudinally extending lines, it will be understood that various patterns such as spots, squares, or transverse lines are suitable. The adhesive employed may be any of the large number of pressure- sensitive adhesives that are commercially available, including water-based adhesives such as acrylate adhesives, e.g., vinyl acetate/2-ethylhexyl acrylate copolymer which may be combined with tackifiers. Alternatively, the adhesive may also comprise a pressure-sensitive rapid-setting hot melt adhesive such as Fuller 6680 produced by the H. B. Fuller Co. The adhesive means may also comprise a double faced tape.

Figure 13:
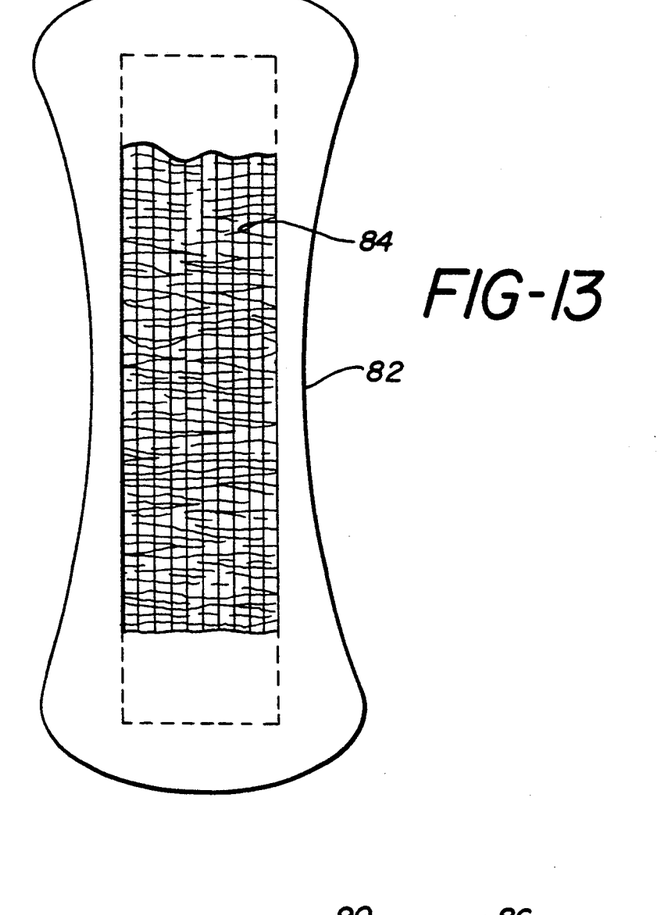
FIG. 13: is a plan view of an ultra-thin sanitary napkin embodiment, illustrating in cut away section, a cut and calendered peat moss board absorbent element.
Figure 14:
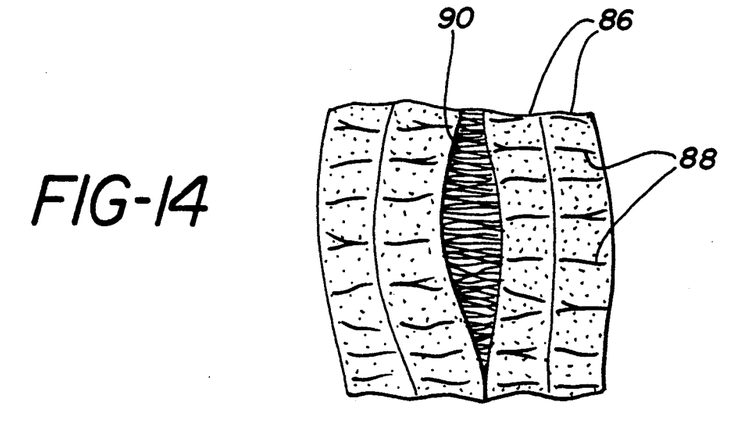
FIG. 14: is an enlarged partial view of the peat moss absorbent element of FIG. 13, illustrating how the longitudinal strips are connected with a fibrous structure.

In another preferred embodiment of this invention described in FIG. 13, an hourglass-shaped, ultra-thin, sanitary napkin 82 is provided having a light-weight construction. In such an embodiment, the C-shaped boat and bulky wood pulp core are eliminated and a longitudinally-cut, absorbent layer 84, having a preferred thickness of less than about 10 mm, preferably less than about 5 mm, is employed. See U.S. patent application Ser. No. 07/242,278, entitled "Unitized Sanitary Napkin", filed on Sep. 12, 1988 now abandoned, and which is hereby incorporated by reference. The preferred absorbent layer 84 of this embodiment includes a plurality of longitudinally extending absorbent strips 86, preferably made of superabsorbent material and/or peat moss. The layer 84 also includes fibrous members 90 for connecting the absorbent strips 86 to one another along their longitudinal sides for maintaining the integrity of the layer 84 during handling, i.e., processing, assembly, and use by the wearer. The layer 84 can also be creped to achieve transverse creases 88 which add more flexibility to the element and attendant comfort to a wearer. The absorbent layer 84 is preferably sandwiched between an embossed fluid permeable cover, such as a non-woven layer of cellulose or polyester-polyethylene congregate fibers, and a polyethylene, fluid impervious barrier. The cover and barrier, which can include constructions and materials previously disclosed above, are then heat or ultrasonically sealed about the periphery of the hourglass-shape to seal in the absorbent layer 84. Flaps can also be provided in this light construction by extending the barrier and cover laterally from the central absorbent and then heat sealing and cutting these members in the form of flaps. The construction thus described is substantially thinner than the conventional sanitary napkin described earlier, and can be an attractive alternative product.

The foregoing demonstrates that the mechanical attachment mechanisms of this invention can provide securement of sanitary napkins to undergarments for minimizing shifting during movements by a wearer. These mechanisms can be favorably employed with ultra-thin sanitary napkins without the art-recognized bunching and twisting associated with employing only adhesive strips. Although various embodiments have been illustrated, this was for the purpose of describing, but not limiting the invention. Various modifications, which will become apparent to one skilled in the art, are within the scope of this invention described in the attached claims.

List of Reference Numerals 14 undergarment
16 sanitary napkin
17 radial slits
18 apertured retainer ring
19 circular aperture
20 circular protruding button
22 undergarment-facing side
24 body-facing side
28 flexible strap
30 button portion
32 recess
34 absorbent material
36 circular tape
38 adhesive element
40 break-off tab
42 circular protruding button
44 female portion
46 radial slits
48 circular aperture
50 adhesive
52 female portion
54 circular aperture
56 radial slits
58 elastic cord
60 circular protruding button
62 female fastening element
64 restrictive portion
66 receiving portion
68 circular protruding button
70 male fastening element
72 female fastening element
74 flexible strap
76 female fastening element
78 male fastening element
80 flexible strap
82 sanitary napkin
84 absorbent layer
86 longitudinally extending absorbent strips
88 creases
90 fibrous members

We claim:

1. A sanitary napkin comprising a central absorbent element having longitudinally extending sides, transverse ends, a body-facing side and an undergarment-facing side, said central absorbent element including mechanical attachment means for directly securing said sanitary napkin to an undergarment, thereby minimizing shifting of said sanitary napkin during movements by a wearer, said mechanical attachment means comprising (i) first and second fastening elements which engage to capture a portion of said undergarment therebetween and (ii) means for affixing said first fastening element directly to said central absorbent element.

2. The sanitary napkin of claim 1 comprising a break-off tab, said break-off tab forming at least a portion of said male or female fastening elements.

3. The sanitary napkin of claim 1 wherein said mechanical attachment means comprises a slide fastener in which said male fastening element comprises a circular protruding button and said female fastening element comprises aperture means for receiving and slidable engaging said circular protruding button.

4. The sanitary napkin of claim 1 wherein said mechanical attachment means comprises a snap fastener.

5. The sanitary napkin of claim 1 wherein said second fastening element is affixed to a flexible retainer means which extends laterally from one of said longitudinally extending sides or transverse ends.

6. The sanitary napkin of claim 5 wherein said flexible retainer means comprises an elastic cord.

7. The sanitary napkin of claim 5 wherein said flexible retainer means comprises a thermoplastic strap.

8. The sanitary napkin of claim 7 wherein said strip comprises a polyethylene web.

9. The sanitary napkin of claim 1 wherein said first fastening element comprises first and second portions forming a recess therebetween for retaining said captured portion of said undergarment.

10. The sanitary napkin of claim 9 wherein said first fastening element affixing means for affixing said first fastening element to said central absorbent element so that said first portion of said first fastening element is held in contact with said central absorbent element.

11. The sanitary napkin of claim 9 wherein said first fastening element affixing means comprises said first portion of said first fastening element.

12. The sanitary napkin of claim 11 wherein said first fastening element affixing means further comprises adhesive means.

13. The sanitary napkin of claim 9 wherein said first and second fastening elements comprise male and female elements, respectively.

14. The sanitary napkin of claim 13 wherein said second portion of said first fastening element comprises a button and said second fastening element comprises a ring.

15. A sanitary napkin comprising a central absorbent element having longitudinally extending sides, transverse ends, a body-facing side and an undergarment-facing side, said central absorbent element including mechanical attachment means attached directly to the undergarment-facing side of said central absorbent element for securing said sanitary napkin to an undergarment for minimizing shifting of said sanitary napkin during movements by a wearer, said mechanical attachment means comprising male and female fastening elements which engage to capture a portion of said undergarment wherein one of said male and female fastening elements is affixed to said undergarment-facing side of said central absorbent element, and wherein one of said male and female fastening elements is affixed to a flexible retainer means which extends laterally from one of said longitudinally extending sides or transverse ends, said flexible retainer means comprising an elastic cord and wherein said male fastening element comprises a circular protruding button and said female fastening element comprises tab means, said tab means having a circular aperture and a plurality of radial slits extending outwardly from said circular aperture for snugly receiving said circular protruding button.

16. A sanitary napkin comprising a central absorbent element having longitudinally extending sides, transverse ends, a body-facing side and an undergarment-facing side, said central absorbent element including mechanical attachment means for securing said sanitary napkin to an undergarment for minimizing shifting of said sanitary napkin during movements by a wearer, said mechanical attachment means comprising male and female fastening elements which engage to capture a portion of said undergarment, at least one of said male and female fastening element being permanently affixed to said undergarment-facing side of said central absorbent and one of said male and female fastening elements being affixed to a flexible retainer means which extends laterally from one of said longitudinally extending sides or transverse ends.

17. A sanitary napkin of claim 16 wherein said flexible retainer means comprises a strap comprising a polyethylene web.

18. A sanitary napkin comprising a central absorbent element having longitudinally extending sides, transverse ends, a body-facing side and an undergarment-facing side, said central absorbent element including mechanical attachment means for securing said sanitary napkin to an undergarment for minimizing shifting of said sanitary napkin during movements by a wearer, said mechanical attachment means comprising male and female fastening elements which engage to capture a portion of said undergarment, at least one of said male and female fastening elements being affixed to said undergarment-facing side of said central absorbent and one of said male and female fastening elements being affixed to a flexible retainer means which extends laterally from one of said longitudinally extending sides or transverse ends, said flexible retainer means comprising a strap comprising a polyethylene web and wherein said fastening element comprises a circular protruding button and said female fastening element comprises:
 a circular aperture for snugly receiving said portion of the thickness of said undergarment and said circular protruding button; and
 a plurality of radial slits extending outwardly from said circular opening.

19. A sanitary napkin comprising:
(a) a central absorbent element having an absorbent layer therein, said layer having an initial structural integrity and including a plurality of longitudinally extending absorbent strips disposed adjacent to one another, said layer further including fibrous means for connecting said absorbent strips to one another for maintaining the structural integrity of said element during handling;
(b) a body fluid pervious surface disposed on a body-facing side of said central absorbent element;
(c) a body fluid impervious surface disposed on an undergarment-facing side of said central absorbent element; and
(d) mechanical attachment means affixed to said sanitary napkin, said mechanical attachment means comprising male and female fastening elements which engage to capture a portion of said undergarment.

20. The sanitary napkin of claim 19 wherein said strips comprise cut and calendered peat moss board portions.

21. The sanitary napkin of claim 20 wherein one of said male and female fastening elements is affixed to said body fluid impervious surface of said central absorbent element.

22. The sanitary napkin of claim 21 wherein one of said male and female fastening elements is affixed to a flexible retainer means which extends laterally from said central absorbent element.

23. A sanitary napkin comprising:
(a) a central absorbent element having an absorbent layer therein, said layer having an initial structural integrity and including a plurality of longitudinally extending peat moss strips disposed adjacent to one another, said layer further including fibrous means for connecting said strips to one another for maintaining the structural integrity of said element during handling;

(b) a body fluid impervious surface disposed on a body-facing side of said central absorbent element;

(c) a body fluid impervious surface disposed on an undergarment-facing side of said central absorbent element; and (d) mechanical attachment means affixed to said sanitary napkin, said mechanical attachment means comprising male and female fastening elements which engage to capture a portion of said undergarment.

wherein one of said male and female fastening elements is affixed to said body fluid impervious surface of said central absorbent, and one of said male and female fastening elements is affixed to a flexible retainer strap which extends laterally from said central absorbent element.

24. A method of securing a sanitary napkin to an undergarment, comprising:

(a) providing a sanitary napkin including a central absorbent element having a body-facing side and an undergarment-facing side, said central absorbent element including mechanical attachment means affixed thereon, said mechanical attachment means comprising male and female fastening elements;

(b) disposing said sanitary napkin onto an interior surface of an undergarment; and (c) engaging said male and female fastening elements through a portion of said undergarment so as to secure said sanitary napkin to said undergarment for minimizing shifting of said sanitary napkin during movements by a wearer.

25. The method of claim 24, wherein said mechanical attachment means comprises a plurality of pairs of male and female fastening elements, wherein at least a portion of said elements are affixed to said undergarment-facing side of said central absorbent.

* * * * *